United States Patent [19]

Barnett

[11] Patent Number: 5,486,879
[45] Date of Patent: Jan. 23, 1996

[54] PORTABLE, PUBLIC USE READING GLASSES EYE TESTER

[76] Inventor: Mark Barnett, 2260 El Cajon Blvd. #119, San Diego, Calif. 92104

[21] Appl. No.: 254,567
[22] Filed: Jun. 6, 1994
[51] Int. Cl.⁶ ........................................................ A61B 3/02
[52] U.S. Cl. ............................ 351/223; 351/234; 351/239
[58] Field of Search ..................................... 351/200, 222, 351/223, 225, 227, 229, 234, 239

[56] References Cited

U.S. PATENT DOCUMENTS

| 1,384,252 | 7/1921 | Giddens | 351/223 |
| 4,896,959 | 1/1990 | O'Brien | 351/222 |

Primary Examiner—Anita Pellman Gross
Assistant Examiner—Huy Mai

[57] ABSTRACT

Two identical plates somewhat in the shape of very large eyeglass frames sandwiching two rotable discs, one for each eye, form the front section of the device. Each disc has a series of magnifying lenses of increasing power which can be brought into the eye openings in the plate when the discs are rotated and allow the user to focus on a group of alphbetical characters of a predetermined size and at a predetermined distance from the lenses at the end of a view tunnel. The strength of the lenses required for focusing can then be read from the disc where it is clearly indicated next to each lens. These lens strengths correspond to the power of reading glasses sold non-prescription in most drug stores.

5 Claims, 4 Drawing Sheets 5,486,879

PORTABLE, PUBLIC USE READING GLASSES EYE TESTER

BACKGROUND OF THE INVENTION

The present invention relates to an eye testing device that can easily be used by anyone to test their own eyes. More it relates in particular to an eye testing device to test an individuals need or requirements for reading glasses

PRIOR ART

Most people at some time after the age of forty experience an increasing inability to focus on near objects. Though of otherwise normal vision, they find they can no longer read without the help of magnifying lenses (reading glasses).

While there have been numerous devices patented to test eyes, they have been intended for professional use only. Furthermore, they have been developed to test the full range of eye disorders and usually included a complicated set of levers, lenses, lights and other additions to accomplish the task. One of the simpler such devices, Giddons, July 1921 U.S. Pat. No. 1,384,252, employed a number of discs in tandem along with a number of levers and lenses to test eyes, and was, of course, intended for professional use There appears to be no eye testing device on record, however, soley intended to test for reading glasses requirements and at the same time intended for self-testing by the public.

SUMMARY OF THE INVENTION

The object of this device is to provide a simple, easily used and understood, portable, public or non-professional operated eye tester for those people seeking to determine their requirements for reading glasses.

The device has two identical plates sandwiching two rotable discs comprising the front section. These plates are shaped roughly like two very large eye glass frames with openings for the eyes and a space between and below for the nose. The two sandwiched discs, one for each eye, have a series of magnifying lenses of increasing strength which can be brought into the plates eye openings by turning the the discs for each eye independently. Attached to the back of the front section is a view tunnel at the end of which is a series of characters or numerals at a predetermined distance from the lenses. By looking through the eyes holes in the front section at the characters at the end of the view tunnel and adjusting the discs until lenses are found that bring the characters into focus, the user can then determine the strength of the reading glasses needed by reading the power of the lens which is indicated on the disc next to the respective lens and clearly visible through the front plate eye opening.

DETAILED DESCRIPTION

Figure 1:
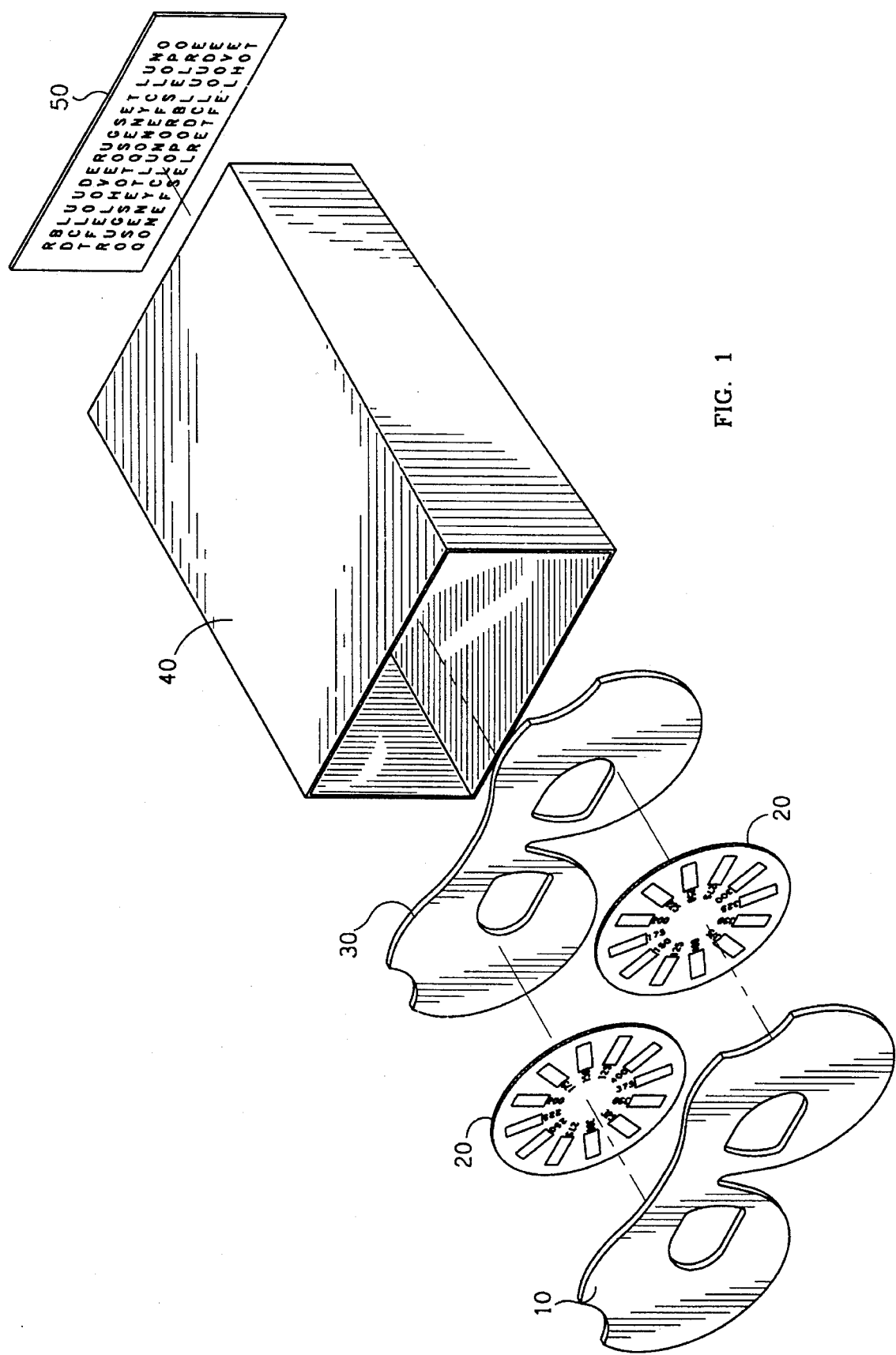
FIG. 1 Top front perspective of the preferred embodiment of the invention showing all pieces in order of assembly.
Figure 2:
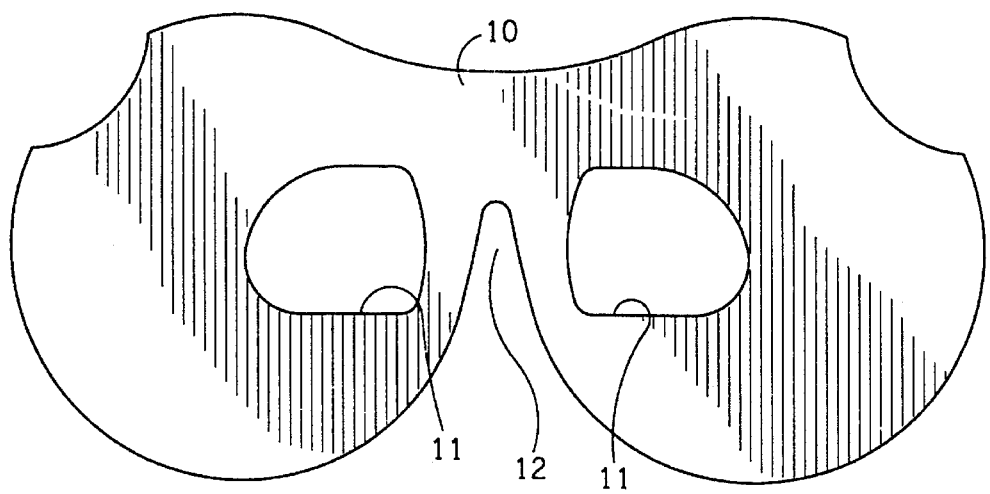
FIG. 2 Enlarged front perspective of front section view plate
Figure 3:
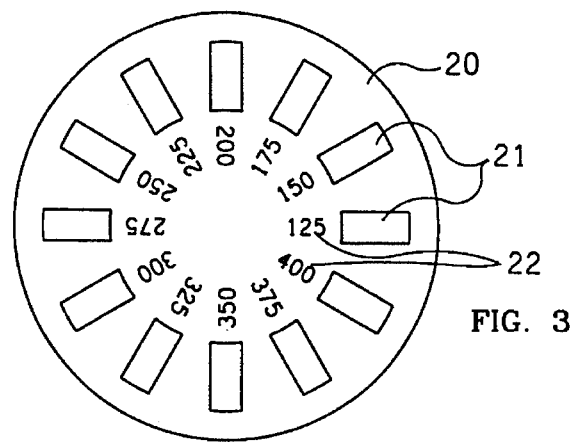
FIG. 3 Enlarged front perspective of disc with magnifying lenses
Figure 4:
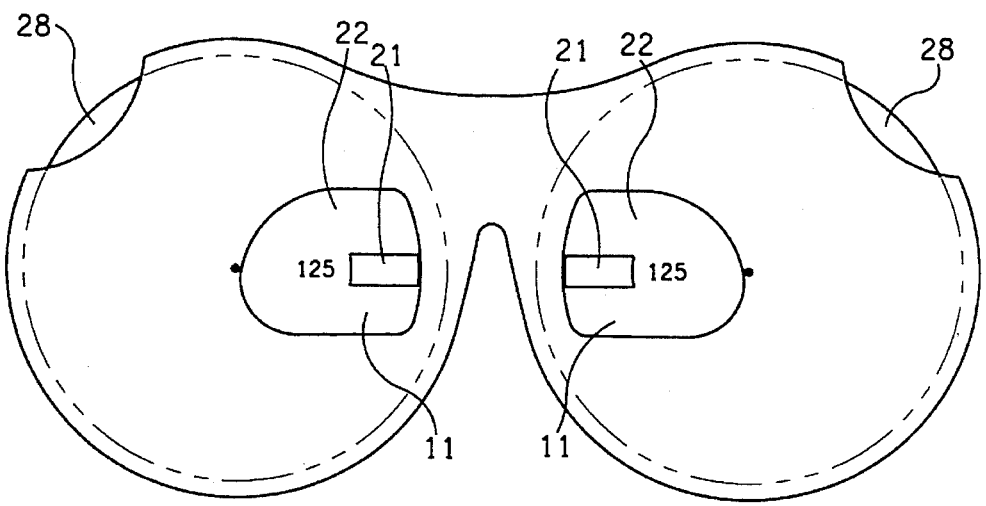
FIG. 4 Assembled front section

In the accompanying drawings, FIG. 1 is an overview of the preferred embodiment of the invention. The parts are shown in order of assembly with the two main sections identified. FIG. 2 is an enlargement of the view plates 10 and 30 (they are identical) shown in FIG. 1. Each view plate is a frame with two holes or eye openings cut out 11, one for each eye, and an indentation. 12 between and below for the nose. One view plate forms the first part of the front section. Forming the second part are two discs. FIG. 3 is an enlargement of one of the disc 20 first shown in FIG. 1 (both discs are identical) and shows a series of lenses which are of increasing magnification from 1.25 power up to 4 power. The lenses 21, are implaced clocklike around the outer edges of the disc 20. The power of each lens is indicated next to each lens on the inner part 22 of the disc 22. The discs are rotably mounted behind one view plate and then sandwiched by a second view plate to form the front section shown in FIG. 4. The discs are of a size so that the lenses and their indicated power are clearly visible through view plate eye openings. The discs are rotated by turning them at the upper outer corners of the plates where there is a indentation 28 for this purpose.

Figure 5:
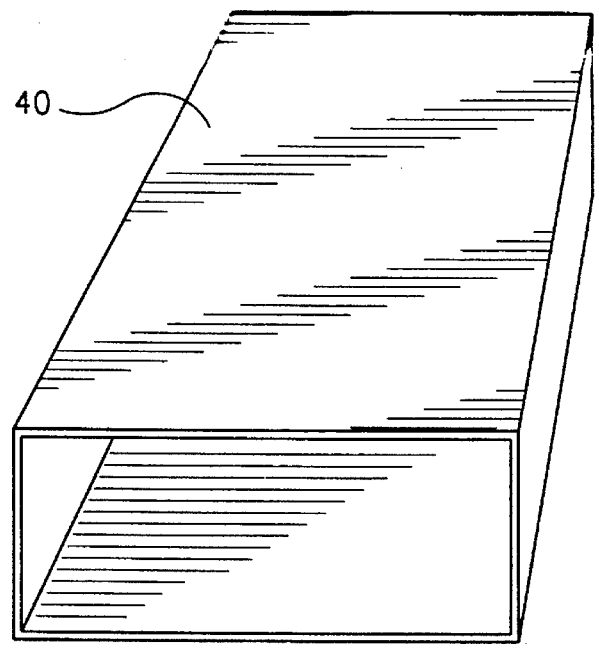
FIG. 5 Top front perspective of view tunnel
Figure 6:
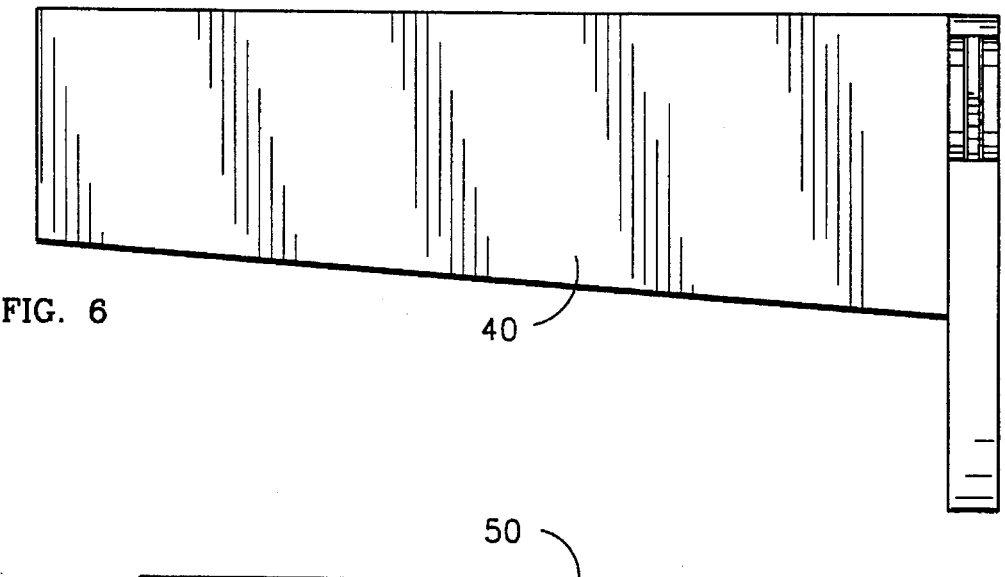
FIG. 6 Side perspective of view tunnel attached to front section

Just two pieces make up the second section of the invention. FIG. 5 is an enlarged perspective of the view tunnel, 40 first shown in FIG. 1. It is an elongated chamber or box open at both ends 41 and 43 which serves as a view tunnel when it is attached to the back of the rear plate of the front section as seen in FIG. 6, which is a side perspective.

Figure 7:
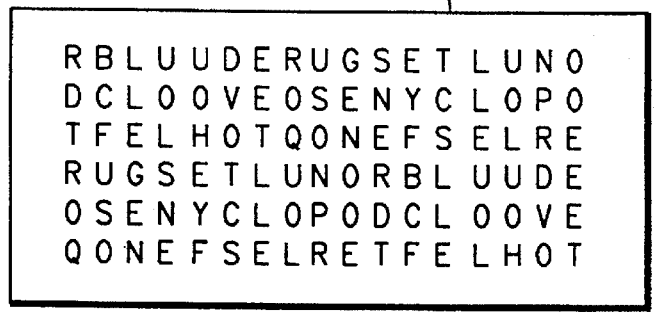
FIG. 7 Enlarged front perspective of end plate

Returning to FIG. 1 and the overview of all the pieces, for assembly, one open end of the view tunnel 40 is attached so that an open end is lined up with the eye holes 11 of the front section thus permitting a clear field of view through the front view plate 10, disc lenses 21, rear view plate 30, into the attached view tunnel 40 and out the far open end. Finally, the end plate 50 is attached. FIG. 7 is an enlarged frontal view of this end plate 50 first shown in FIG. 1. It is a piece of clear or opaque rigid material which is light permeable. It has alphabetical or numerical characters of a predetermined size mounted on it and is attached to the far end of the view tunnel 40 at a predetermined distance from the lenses of the front section.

To use this hand-held portable, public or non-professional use eye testing device to determine reading glasses requirements, it is held by the user or self tester to the eyes to look through the view plate eye openings 11 at the characters at the far end of the view tunnel 40. The lenses 21 can then be adjusted or changed as in this embodiment they are mounted on discs 20 and the discs can be rotated independently for each eye, to bring the characters on the end plate 50 into focus. The magnifying power of the lenses 21 can then be read from each disc where they are indicated 22 next to the lenses and clearly visible through the front plate eye openings.

Figure 8:
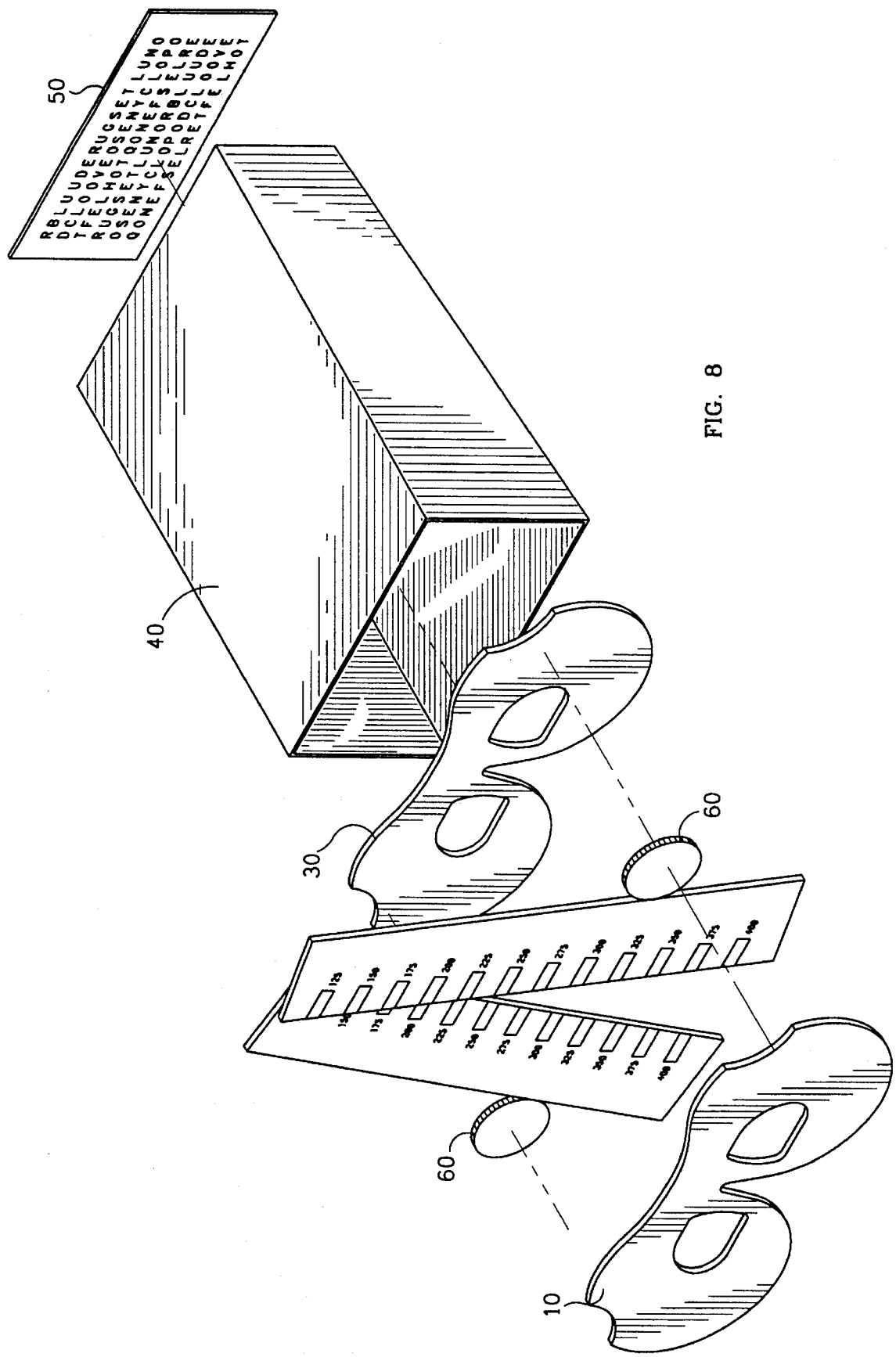
FIG. 8 Top front perspective showing all the pieces in order of assembly with the geared disc and rod variation

Alternatively, as shown in FIG. 8, instead of mounting the lenses on two rotating discs as described above, there would be two smaller rotable discs with geared edges which would intermesh with two rods with geared edges. The rods would have magnifying lenses mounted in a ladderlike configuration and the lenses would be presented to the eye openings in the view plates when the smaller discs were rotated, this would cause the rods to move up or down accordingly. In all other aspects, the eye testing device would remain the same as described in the preferred embodiment described earlier.

To briefly summarize, the invention is a self-testing device designed to allow those in need of reading glasses to determine the magnification power of the lenses needed. Essentially, the device is just a frame holding a series of magnification lenses a predetermined distance from a series of alphabetical or numerical characters of a predetermined size and a method or way to then adjust or change the lenses presented to the users eyes in order to bring the characters into focus. The power of the lenses required for focusing can then be determined from the power indicated next to each lens. These indicated powers correspond to the indicated powers of reading glasses which are sold over-the-counter or non-prescription in most drugstores.

The foregoing description of the preferred embodiment of the invention and one variation have been presented for the purposes of illustration and description. They are not intended to be exhaustive or to limit the invention to the precise forms disclosed, Many modifications are possible in the light of the above intentions and it is intended that the scope of the invention not be limited by the above detailed description.

I claimed:

1. A portable public use reading glasses eye tester comprising:
   a. a front section comprising 2 view plates with openings for two eyes and an indentation for a nose sandwiching two series of non prescription reading glass magnification lenses of increasing power, one series for each eye, and means for a user to adjust the lenses independently for each eye, and
   b. a rear section view tunnel with 2 open ends, a first open end attached to said front section and at a second open end a series of characters of predetermined size mounted on an end plate of light permeable rigid material at a predetermined distance from the lenses of the front section.

2. A portable public use reading glasses eye tester described in claim 1 having only two series of lenses, said lenses are reading glass magnification lenses and wherein said magnification lenses are implaced on only 2 rotable discs, only one series of said lenses on one disc and only one disc for each eye and whereby said user may adjust said lenses by rotating said discs to bring each lens in turn into said view plate eye openings.

3. A portable public use reading glasses eye tester described in claim 1 wherein said magnification lenses are implaced on 2 geared rods, each rod having one series of lenses and one rod for each eye and whereby said user may adjust said rods by rotating 2 small geared discs which are intermeshed with said geared rods thereby moving said rods up or down to bring each lens in turn into said view plates eye openings.

4. A portable public use reading glasses eye tester comprising:
   a. Two view plates each with 2 eye openings and a nose indentation attached to one of two ends of an elongated open-ended hollow view tunnel of predetermined length
   b. 2 series of non-prescription reading glass magnification lenses of increasing power, one series for each eye, sandwiched between said view plates
   c. a light-permeable rigid end plate attached to a second of said two open ends of said elongated view tunnel
   d. characters of a predetermined size mounted on said end plate, and
   e. means by which a user, looking through said view plates may adjust said manification lenses to bring said characters mounted on said end plate into said user's focus.

5. A portable, public or non-professional use eye tester to determine reading glasses requirements comprising a front view plate which is a frame with eye openings for each eye and an indentation between and below for a nose, only 2 discs, one for each eye, each with a series of non prescription reading glass magnification lenses of increasing power implaced clocklike around said discs outer edges and said lenses of a size so they are clearly visible through said front view plate eye openings when said discs are rotably mounted behind said front view plate and sandwiched by a second identical view plate and said discs are rotated by a user to line up lens with a view plate eye opening, look through said opening and lens into a view tunnel which is an elongated hollow chamber of pre determined length open at both ends, one open end attached to said second view plate and lined up with said view plate eye openings permitting a clear field of view to a second open end of said view tunnel where there is an end plate of light permeable rigid material on which are mounted a series of characters (or both) of a predetermined size.

\* \* \* \* \*